(12) United States Patent
Ries et al.

(10) Patent No.: US 8,065,007 B2
(45) Date of Patent: Nov. 22, 2011

(54) METHOD AND APPARATUS FOR FORMING A HERMETIC ENCLOSURE SEAL IN AN IMPLANTABLE MEDICAL DEVICE

(75) Inventors: Andrew J. Ries, Lino Lakes, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 1664 days.

(21) Appl. No.: 11/364,262

(22) Filed: Feb. 28, 2006

(65) Prior Publication Data
US 2006/0259091 A1 Nov. 16, 2006

Related U.S. Application Data

(60) Provisional application No. 60/681,406, filed on May 16, 2005.

(51) Int. Cl.
*A61N 1/375* (2006.01)
(52) U.S. Cl. ......................................................... 607/36
(58) Field of Classification Search ................. 607/2, 36
See application file for complete search history.

(56) References Cited

U.S. PATENT DOCUMENTS

| 4,399,819 A | | 8/1983 | Cowdery | |
|---|---|---|---|---|
| 4,441,498 A | * | 4/1984 | Nordling | 607/32 |
| 4,785,827 A | | 11/1988 | Fischer | |
| 5,031,791 A | * | 7/1991 | Serio, Jr. | 220/281 |
| 5,456,698 A | * | 10/1995 | Byland et al. | 607/36 |
| 5,535,097 A | | 7/1996 | Ruben et al. | |
| 6,272,382 B1 | | 8/2001 | Faltys et al. | |
| 6,522,915 B1 | * | 2/2003 | Ceballos et al. | 600/509 |
| 6,788,974 B2 | * | 9/2004 | Bardy et al. | 607/36 |
| 2004/0215280 A1 | | 10/2004 | Dublin et al. | |

FOREIGN PATENT DOCUMENTS

| EP | 534782 A | 3/1993 |
|---|---|---|
| WO | WO0234333 A | 5/2002 |

OTHER PUBLICATIONS

International Search Report, PCTUS/2006/018825, Oct. 16, 2006, 6 pages.

* cited by examiner

*Primary Examiner* — Niketa Patel
*Assistant Examiner* — Alyssa M Alter
(74) *Attorney, Agent, or Firm* — Michael C. Soldner (57) ABSTRACT

An implantable medical device that includes a housing having a first shield having an outwardly extending first flange and a second shield having an outwardly extending second flange. The first flange is fixedly engaged with the second flange along a seal to form a housing flange extending outward from the housing, and a surround shroud, having first recessed portions for receiving the housing flange when the shroud is positioned about the housing.

4 Claims, 6 Drawing Sheets

METHOD AND APPARATUS FOR FORMING A HERMETIC ENCLOSURE SEAL IN AN IMPLANTABLE MEDICAL DEVICE

RELATED APPLICATION

The present application claims priority and other benefits from U.S. Provisional Patent Application Ser. No. 60/681,406, filed May 16, 2005, entitled "METHOD AND APPARATUS FOR FORMING A HERMETIC ENCLOSURE SEAL IN AN IMPLANTABLE MEDICAL DEVICE", incorporated herein by reference in its entirety.

FIELD OF THE INVENTION

The present invention generally relates to implantable medical devices, and more particularly, to a method and apparatus for forming a hermetic enclosure seal in an implantable medical device.

BACKGROUND OF THE INVENTION

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the EGM.

The current state of the art of ICDs or implantable pacemaker/cardioverter/defibrillators (PCDs) includes a full featured set of extensive programmable parameters which includes multiple arrhythmia detection criteria, multiple therapy prescriptions (for example, stimulation for pacing in the atrial, ventricular and dual chamber; atrial and ventricular for bradycardia; bi-atrial and/or bi-ventricular for heart failure; and arrhythmia overdrive or entrainment stimulation) and high level stimulation for cardioversion and/or defibrillation, extensive diagnostic capabilities and high speed telemetry systems. These full-featured ICDs or PCDs, hereinafter IMD, are typically implanted into patients who have had, and survived, a significant cardiac event (such as sudden death). Additionally, these devices are expected to last up to 5-8 years and/or provide at least 200 life saving therapy shocks.

Even though there have been great strides in size reduction over the past 20 years, the incorporation of all these features in an IMD, including the longevity requirements, dictates that the devices be typically much larger than current state of the art pacemakers. Such devices are often difficult to implant in some patients (particularly children and thin, elderly patients) and typically require the sacrifice of 1 or 2 veins to implant the lead system because leads associated with the implantation of an IMD utilize a transvenous approach for cardiac electrodes and lead wires. The defibrillator canister/housing is generally implanted as an active can for defibrillation and electrodes positioned in the heart are used for pacing, sensing and detection of arrhythmias.

Although IMDs and implant procedures are very expensive, most patients who are implanted have experienced and survived a sudden cardiac death episode because of interventional therapies delivered by the IMDs. Survivors of sudden cardiac death episodes are in the minority, and studies are ongoing to identify patients who are asymptomatic by conventional measures but are nevertheless at risk of a future sudden death episode. Current studies of patient populations, e.g., the MADIT II and SubQ ICD HeFT studies, are establishing that there are large numbers of patients in any given population that are susceptible to sudden cardiac death, that they can be identified with some degree of certainty and that they are candidates for a prophylactic implantation of a defibrillator (often called primary prevention). However, implanting currently available IMDs in all such patients would be prohibitively expensive. Further, even if the cost factor is eliminated there is shortage of trained personnel and implanting resources.

One option proposed for this patient population is to implant a prophylactic subcutaneous implantable cardioverter/defibrillator (SubQ ICD) such that when these patients receive a shock and survive a cardiac episode, they will ultimately have an implant with a full-featured ICD and transvenous leads. The housing or "can" of the device includes a first shield and a second shield that are joined together by a weld formed along a seam following placement of the internal components within shields to seal device, so that the two shields define an enclosure for the internal components of device. Since the housing is typically positioned subcutaneously in close proximity to the patient's ribs, for example, current configurations for the housing for such devices include the use of non-planar surfaces, such as a concave surface, for example, in order to better enable positioning of the housing in the patient. As a result, there is a need for an improved method and apparatus for forming the weld along the seam of the housing that addresses the non-planar seam weld profile.

BRIEF DESCRIPTION OF THE DRAWINGS

Features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE INVENTION

Figure 1:
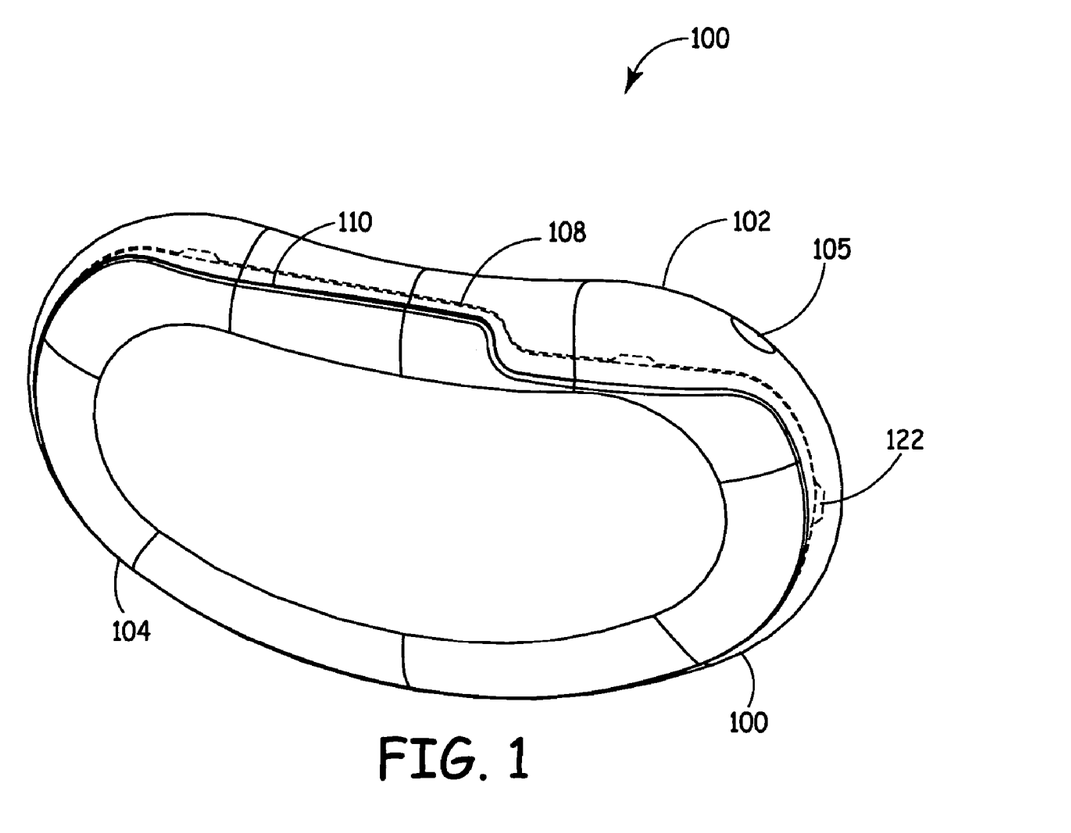
FIG. 1 is a perspective view of an exemplary implantable medical device according to an embodiment of the present invention.

FIG. 1 is a perspective view of an exemplary implantable medical device according to an embodiment of the present invention. As illustrated in FIG. 1, an implantable medical device 100 includes a surround shroud 102 positioned around an outer edge of a housing 104 or "can" of the device 100. The housing 104 includes a first shield 106 and a second shield 108 that are joined together by a weld formed along a seam 110 following placement of the internal components within shields 106 and 108 to seal device 100, so that the two shields 106 and 108 define an enclosure for the internal components of the device 100. A connector port 105 is formed for receiving a connector of a lead (not shown) and electrically coupling the connector to circuitry contained within housing 104.

Housing 104 may be constructed of stainless steel, titanium or ceramic. Surround shroud 102 is formed of polyurethane, polysulfone, epoxy, for example, or other suitable thermoplastic or thermoset polymer. The electronics circuitry of the device 100 may be incorporated on a polyamide flex circuit, printed circuit board (PCB) or ceramic substrate with integrated circuits packaged in leadless chip carriers and/or chip scale packaging (CSP).

The electronic circuitry employed in the device 100 can take any of the known forms that detect a tachyarrhythmia from the sensed EGM and provide cardioversion/defibrillation shocks as well as post-shock pacing as needed, such as a subcutaneous device, for example. A simplified block diagram of such circuitry adapted to function employing the first and second and, optionally, the third cardioversion-defibrillation electrodes as well as the EGM sensing and pacing electrodes described above is set forth in FIG. 2. It will be understood that the simplified block diagram does not show all of the conventional components and circuitry of such ICDs including digital clocks and clock lines, low voltage power supply and supply lines for powering the circuits and providing pacing pulses or telemetry circuits for telemetry transmissions between the ICD and an external programmer or monitor.

Figure 2:
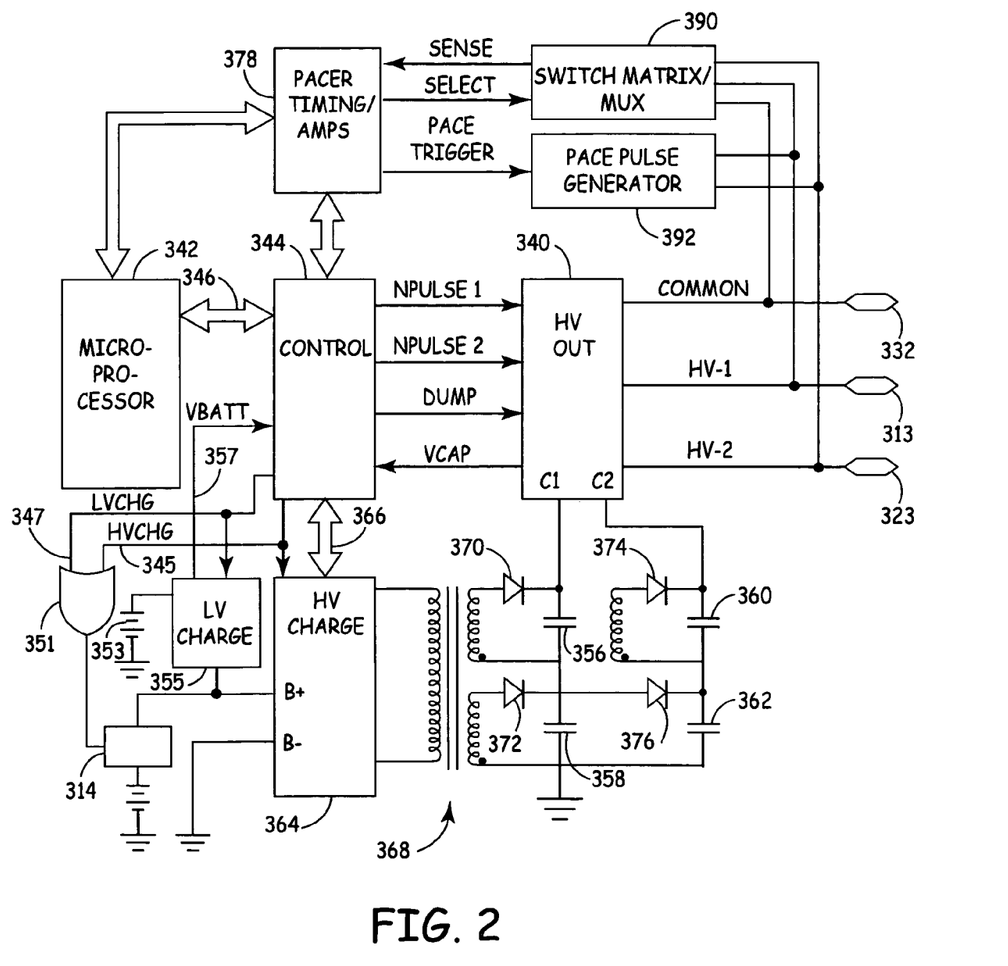
FIG. 2 is an exemplary schematic diagram of circuitry contained within an implantable medical device according to an embodiment of the present invention.

FIG. 2 is an exemplary schematic diagram of circuitry contained within an implantable medical device according to an embodiment of the present invention. As illustrated in FIG. 2, according to an embodiment of the present invention, the device 100 includes a low voltage battery 353 and a high voltage battery 312 positioned within the hermetically sealed housing 104. The low voltage battery 353 is coupled to a power supply (not shown) that supplies power to circuitry of the device 100, including the pacing output capacitors to supply pacing energy in a manner well known in the art. The low voltage battery may include one or two conventional LiCF$_x$, LiMnO$_2$ or LiI$_2$ cells, for example. The high voltage battery 312 may include one or two conventional LiSVO or LiMnO$_2$ cell.

In FIG. 2, SubQ device 100 functions are controlled by means of stored software, firmware and hardware that cooperatively monitor the EGM, determine when a cardioversion-defibrillation shock or pacing is necessary, and deliver prescribed cardioversion-defibrillation and pacing therapies. The block diagram of FIG. 2 incorporates circuitry, such as that set forth in commonly assigned U.S. Pat. No. 5,163,427 "Apparatus for Delivering Single and Multiple Cardioversion and Defibrillation Pulses" to Keimel; U.S. Pat. No. 5,188,105 "Apparatus and Method for Treating a Tachyarrhythmia" to Keimel and U.S. Pat. No. 5,314,451 "Replaceable Battery for Implantable Medical Device" to Mulier, for selectively delivering single phase, simultaneous biphasic and sequential biphasic cardioversion-defibrillation shocks typically employing an Idevice housing electrode coupled to the COMMON output 332 of high voltage output circuit 340 and one or two cardioversion-defibrillation electrodes disposed in a heart chamber or cardiac vessel coupled to the HV1 and HV-2 outputs (313 and 323, respectively) of the high voltage output circuit 340. The circuitry of the subcutaneous device of the present invention can be made simpler by adoption of one such cardioversion-defibrillation shock waveform for delivery simply between the first and second cardioversion-defibrillation electrodes 313 and 323 coupled to the HV-1 and HV-2 outputs respectively. Or, the third cardioversion-defibrillation electrode 332 can be coupled to the COMMON output as depicted in FIG. 2 and the first and second cardioversion-defibrillation electrodes 313 and 323 can be electrically connected in to the HV-1 and the HV-2 outputs, respectively, as depicted in FIG. 2.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The device of the present invention uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation shocks are only delivered when a malignant tachyarrhythmia, e.g., ventricular fibrillation is detected through processing of the far field cardiac EGM employing one of the available detection algorithms known in the art.

In FIG. 2, pacer timing/sense amplifier circuit 378 processes the far field EGM SENSE signal that is developed across a particular EGM sense vector defined by a selected pair of the electrodes 332, 313 and, optionally, electrode 323 if present as noted above. The selection of the sensing electrode pair is made through the switch matrix/MUX 390 in a manner disclosed in the commonly assigned U.S. Pat. No. 5,331,966 "Subcutaneous Multi-Electrode Sensing System, Method and Pacer" to Bennett, et al patent to provide the most reliable sensing of the EGM signal of interest, which would be the R wave for patients who are believed to be at risk of ventricular fibrillation leading to sudden death. The far field EGM signals are passed through the switch matrix/MUX 390 to the input of a sense amplifier in the pacer timing/sense amplifier circuit 378. Bradycardia is typically determined by an escape interval timer within the pacer timing circuit 378 or the timing and control circuit 344, and pacing pulses that develop a PACE TRIGGER signal applied to the pacing pulse generator 392 when the interval between successive R-waves exceeds the escape interval. Bradycardia pacing is often temporarily provided to maintain cardiac output after delivery of a cardioversion-defibrillation shock that may cause the heart to slowly beat as it recovers function.

Detection of a malignant tachyarrhythmia is determined in the timing and control circuit 344 as a function of the intervals between R-wave sense event signals that are output from the pacer timing/sense amplifier circuit 378 to the timing and control circuit 344.

Certain steps in the performance of the detection algorithm criteria are cooperatively performed in a microcomputer 342, including microprocessor, RAM and ROM, associated circuitry, and stored detection criteria that may be programmed into RAM via a telemetry interface (not shown) conventional in the art. Data and commands are exchanged between microcomputer 342 and timing and control circuit 344, pacer timing/amplifier circuit 378, and high voltage output circuit 340 via a bi-directional data/control bus 346. The pacer timing/amplifier circuit 378 and the timing and control circuit 344 are clocked at a slow clock rate. The microcomputer 342 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 378. The algorithms and functions of the microcomputer 342 and timer and control circuit 344 employed and performed in detection of tachyarrhythmias are set forth, for example, in commonly assigned U.S. Pat. No. 5,991,656 "Prioritized Rule Based Apparatus for Diagnosis and Treatment of Arrhythmias" to Olson, et al and U.S. Pat. No. 5,193,535 "Method and Apparatus for Discrimination of Ventricular Tachycardia from Ventricular Fibrillation and for Treatment Thereof" to Bardy, et al, for example. Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '656 and '535 patents.

The detection algorithms are highly sensitive and specific for the presence or absence of life threatening ventricular arrhythmias, e.g., ventricular tachycardia (V-TACH) and ventricular fibrillation (V-FIB). Another optional aspect of the present invention is that the operational circuitry can detect the presence of atrial fibrillation (A FIB) as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm).

Although a subcutaneous device of the present invention may rarely be used for an actual sudden death event, the simplicity of design and implementation allows it to be employed in large populations of patients at modest risk with modest cost by medical personnel other than electrophysiologists. Consequently, the device of the present invention includes the automatic detection and therapy of the most malignant rhythm disorders. As part of the detection algorithm's applicability to children, the upper rate range is programmable upward for use in children, known to have rapid supraventricular tachycardias and more rapid V-FIB.

When a malignant tachycardia is detected, high voltage capacitors 356, 358, 360, and 362 are charged to a pre-programmed voltage level by a high-voltage charging circuit 364. It is generally considered inefficient to maintain a constant charge on the high voltage output capacitors 356, 358, 360, 362. Instead, charging is initiated when control circuit 344 issues a high voltage charge command HVCHG delivered on line 345 to high voltage charge circuit 364 and charging is controlled by means of bi-directional control/data bus 366 and a feedback signal VCAP from the HV output circuit 340. High voltage output capacitors 356, 358, 360 and 362 may be of film, aluminum electrolytic or wet tantalum construction.

The negative terminal of high voltage battery 312 is directly coupled to system ground. Switch circuit 314 is normally open so that the positive terminal of high voltage battery 312 is disconnected from the positive power input of the high voltage charge circuit 364. The high voltage charge command HVCHG is also conducted via conductor 349 to the control input of switch circuit 314, and switch circuit 314 closes in response to connect positive high voltage battery voltage EXT B+ to the positive power input of high voltage charge circuit 364. Switch circuit 314 may be, for example, a field effect transistor (FET) with its source-to-drain path interrupting the EXT B+ conductor 318 and its gate receiving the HVCHG signal on conductor 345. High voltage charge circuit 364 is thereby rendered ready to begin charging the high voltage output capacitors 356, 358, 360, and 362 with charging current from high voltage battery 312.

High voltage output capacitors 356, 358, 360, and 362 may be charged to very high voltages, e.g., 700-3150V, to be discharged through the body and heart between the selected electrode pairs among first, second, and, optionally, third subcutaneous cardioversion-defibrillation electrodes 313, 332, and 323. The details of the voltage charging circuitry are also not deemed to be critical with regard to practicing the present invention; one high voltage charging circuit believed to be suitable for the purposes of the present invention is disclosed. High voltage capacitors 356, 358, 360, and 362 are charged by high voltage charge circuit 364 and a high frequency, high-voltage transformer 368 as described in detail in commonly assigned U.S. Pat. No. 4,548,209 "Energy Converter for Implantable Cardioverter" to Wielders, et al. Proper charging polarities are maintained by diodes 370, 372, 374 and 376 interconnecting the output windings of high-voltage transformer 368 and the capacitors 356, 358, 360, and 362. As noted above, the state of capacitor charge is monitored by circuitry within the high voltage output circuit 340 that provides a VCAP, feedback signal indicative of the voltage to the timing and control circuit 344. Timing and control circuit 344 terminates the high voltage charge command HVCHG when the VCAP signal matches the programmed capacitor output voltage, i.e., the cardioversion-defibrillation peak shock voltage.

Timing and control circuit 344 then develops first and second control signals NPULSE 1 and NPULSE 2, respectively, that are applied to the high voltage output circuit 340 for triggering the delivery of cardioverting or defibrillating shocks. In particular, the NPULSE 1 signal triggers discharge of the first capacitor bank, comprising capacitors 356 and 358. The NPULSE 2 signal triggers discharge of the first capacitor bank and a second capacitor bank, comprising capacitors 360 and 362. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 344 serves to control operation of the high voltage output stage 340, which delivers high energy cardioversion-defibrillation shocks between a selected pair or pairs of the first, second, and, optionally, the third cardioversion-defibrillation electrodes 313, 323, and 332 coupled to the HV-1, HV-2 and optionally to the COMMON output as shown in FIG. 21.

Thus, device 100 monitors the patient's cardiac status and initiates the delivery of a cardioversion-defibrillation shock through a selected pair or pairs of the first, second and third cardioversion-defibrillation electrodes 313, 323 and 332 in response to detection of a tachyarrhythmia requiring cardioversion-defibrillation. The high HVCHG signal causes the high voltage battery 312 to be connected through the switch circuit 314 with the high voltage charge circuit 364 and the charging of output capacitors 356, 358, 360, and 362 to commence. Charging continues until the programmed charge voltage is reflected by the VCAP signal, at which point control and timing circuit 344 sets the HVCHG signal low terminating charging and opening switch circuit 314. Typically, the charging cycle takes only fifteen to twenty seconds, and occurs very infrequently. The device 100 can be programmed to attempt to deliver cardioversion shocks to; the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 100 on a prophylactic basis would be instructed to report each such episode to the attending physician for further evaluation of the patient's condition and assessment for the need for implantation of a more sophisticated and long-lived device.

According to an embodiment of the present invention, device 100 may include a level crossing detection system and process, such as set forth in commonly assigned U.S. patent application Ser. No. 11/114,462, to Ghanen et al., filed Apr. 25, 2005, incorporated herein by reference in it's entirety, to detect noise, sinus rhythm and ventricular fibrillation in subcutaneous or body surface signals to deliver therapies as needed.

Figure 3A:
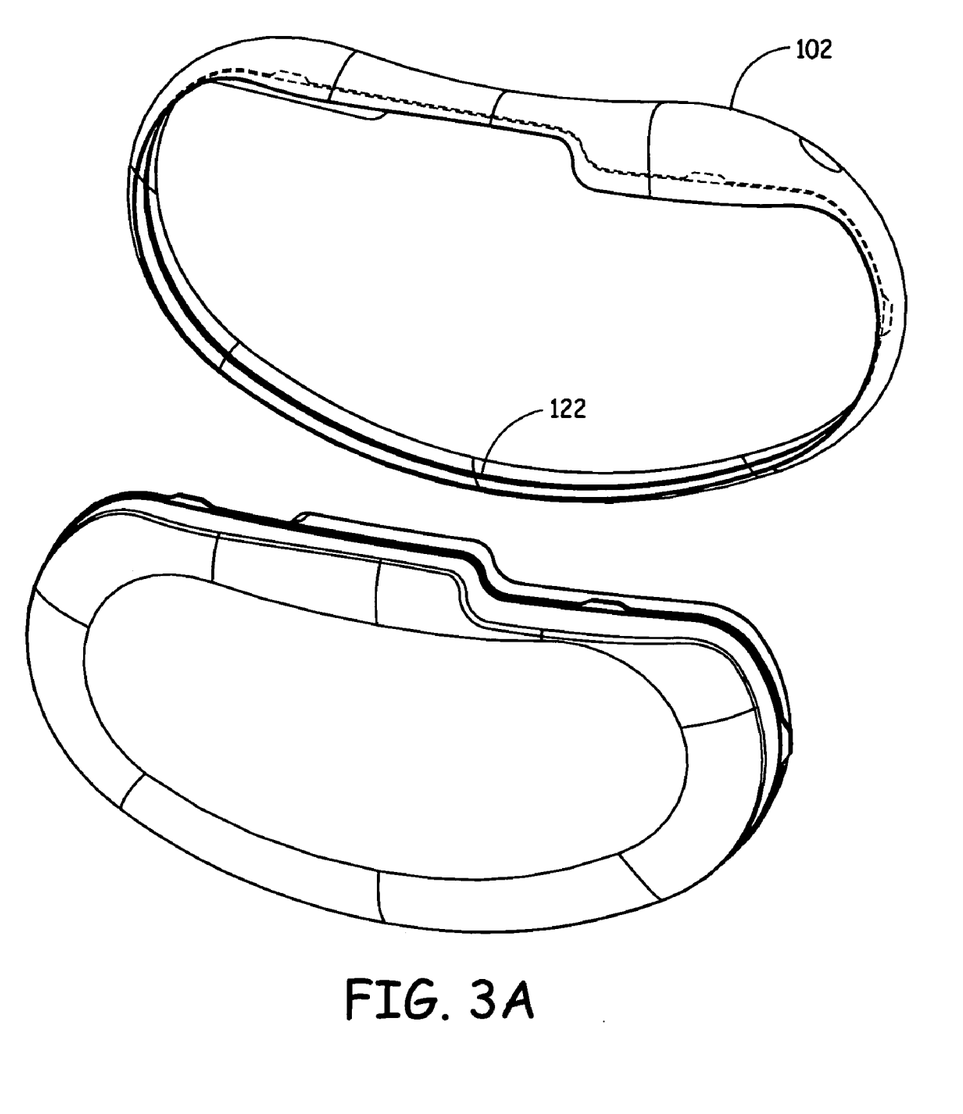
FIG. 3A is a schematic diagram of the implantable medical device of FIG. 1 with the surround shroud separated from the housing body of the device.
Figure 3B:
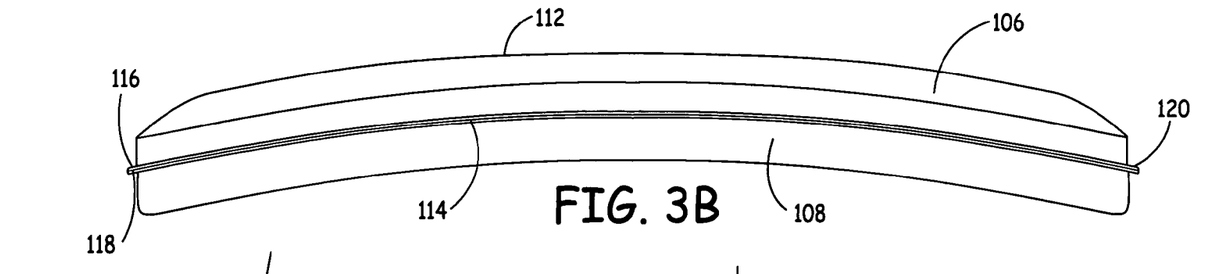
FIG. 3B is a side view of a housing of an implantable medical device according to the present invention.
Figure 3C:
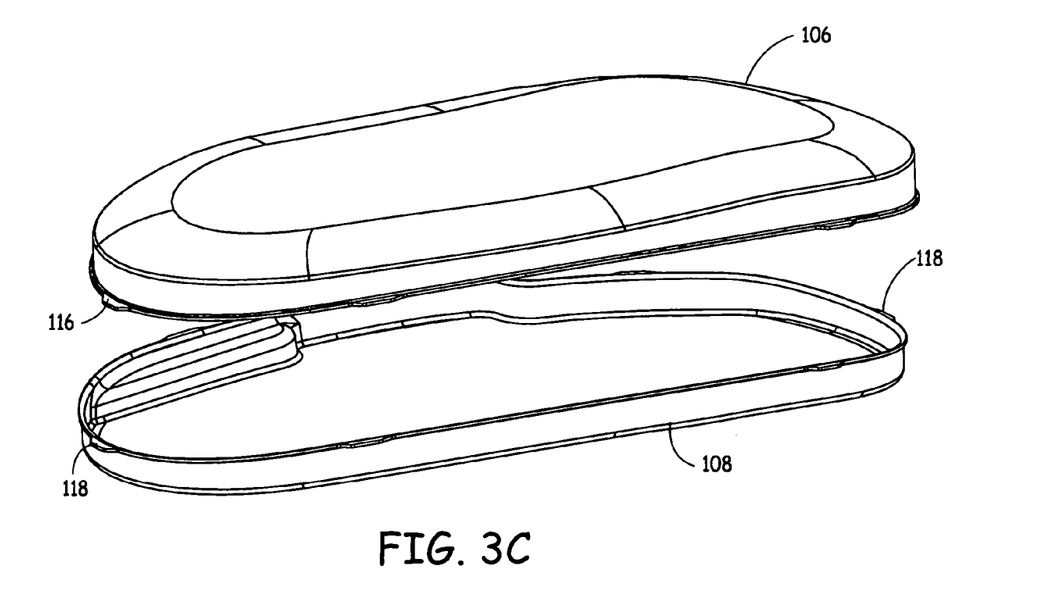
FIG. 3C is a schematic diagram of two separated shields of the device of FIG. 3B.
Figure 3D:
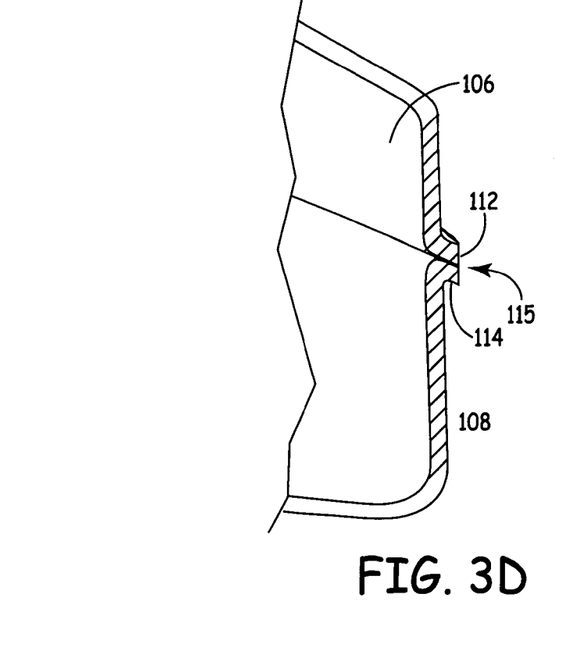
FIG. 3D is a cross-sectional view of a housing, illustrating flanges forming a flange portion according to an embodiment of the present invention.
Figure 3E:
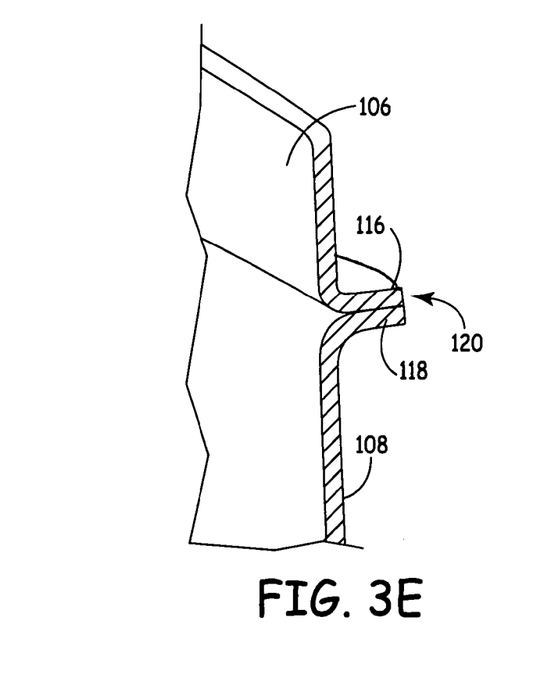
FIG. 3E is a cross-sectional view of a housing, illustrating extended portions of flanges forming tabs according to an embodiment of the present invention.
Figure 3F:
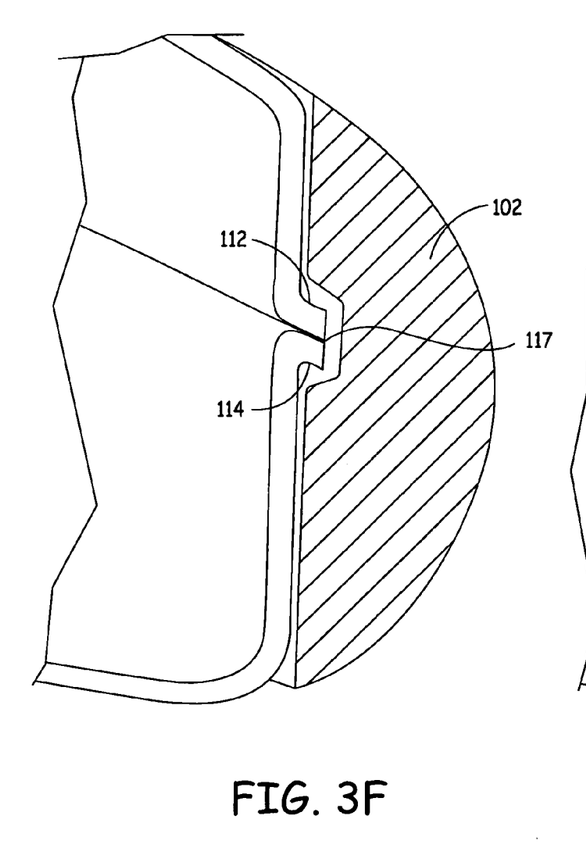
FIGS. 3F and 3G are cross-sectional views of a housing and a surround shroud positioned according to an embodiment of the present invention.
Figure 3G:
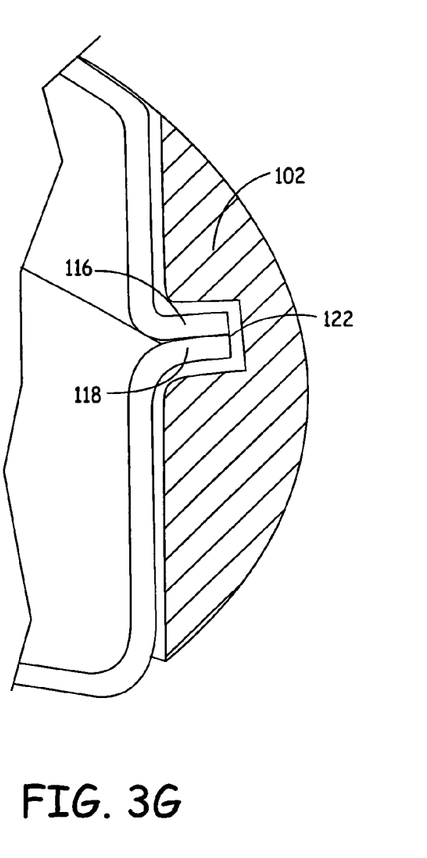

FIG. 3A is a schematic diagram of the implantable medical device of FIG. 1 with the surround shroud separated from the housing body of the device. FIG. 3B is a side view of a housing of an implantable medical device according to the present invention. FIG. 3C is a schematic diagram of two separated shields of the device of FIG. 3B. FIG. 3D is a cross-sectional view of a housing, illustrating flanges forming a flange portion according to an embodiment of the present invention. FIG. 3E is a cross-sectional view of a housing, illustrating extended portions of flanges forming tabs according to an embodiment of the present invention. FIGS. 3F and 3G are cross-sectional views of a housing and a surround shroud positioned according to an embodiment of the present invention.

As illustrated in FIGS. 3A-3G, first shield 106 and second shield 108 forming the housing 104 of the implantable medical device 100 each include a flange portion 112 and 114, respectively, having surfaces extending outward from housing 100 that come into contact and are joined at seal 110 when first shield 106 and second shield 108 are joined together to form the enclosure. As illustrated in FIG. 3B, shields 106 and 108 are formed so that housing 104 has a generally non-planar shape, such as concave shape for example, so that the flange portions 112 and 114 are shaped in a complimentary non-planar fashion along seal 110. Flange portions 112 and 114 come into contact to form a housing flange 115 that extends outward from the housing 104 and is received within recessed portions 117 formed in surround shroud 102 once surround shroud 102 is positioned around the housing 104. In addition, flange portions 112 and 114 include respective extended portions 116 and 118 that come into contact to form one or more tabs 120 that extend outward from flange portions 112 and 114 to be positioned within recessed portions 122 (see FIG. 1) formed in surround shroud 102 once surround shroud 102 is positioned around the housing 104.

It will be apparent from the foregoing that while particular embodiments of the invention have been illustrated and described, various modifications can be made without departing from the spirit and scope of the invention. For example, while the device 100 is described as being a subcutaneous device, the present invention is not intended to be limited to use in subcutaneous devices, but may also be utilized in any devices that detect a tachyarrhythmia from the sensed EGM and provide cardioversion/defibrillation shocks as well as post-shock pacing as needed. Accordingly, it is not intended that the invention be limited, except as by the appended claims.

What is claimed is:

1. An implantable medical device, comprising:
   a housing having a first shield having an outwardly extending first flange and a second shield having an outwardly extending second flange, the first flange fixedly engaged with the second flange to form a housing flange extending outward from and sealing the housing;
   circuitry positioned within the housing;
   a surround shroud having first recessed portions for receiving the housing flange when the shroud is positioned about the housing;
   a first extended portion extending outward from the first flange; and
   a second extended portion extending outward from the second flange, the second extended portion aligned with the first extended portion to form a tab positioned within a second recessed portion formed in the shroud when the shroud is positioned about the housing, wherein the first shield and the second shield are generally non-planar.

2. The device of claim 1, wherein the circuitry is configured to detect a tachyarrhythmia from a sensed EGM and provide one of a cardioversion shock, a defibrillation shock, or post-shock pacing in response to the sensed EGM.

3. The device of claim 2, wherein the device is a subcutaneous device.

4. The device of claim 1, wherein the first extended portion is one of a plurality of first extended portions extending outward from the first flange, and wherein the second extended portion is one of a plurality of second extending portions extending outward from the second flange, the second extending portions aligned with the first extending portions to form a plurality of tabs positioned within a plurality of second recessed portions formed in the shroud, one of which is the second recessed portion, when the shroud is positioned about the housing.

* * * * *